(12) United States Patent
Parrish

(10) Patent No.: US 10,641,763 B2
(45) Date of Patent: May 5, 2020

(54) PREDICTION OF FERTILITY IN MALES

(71) Applicant: WISCONSIN ALUMNI RESEARCH FOUNDATION, Madison, WI (US)

(72) Inventor: John Parrish, Mount Horeb, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/359,558

(22) Filed: Mar. 20, 2019

(65) Prior Publication Data

US 2019/0219567 A1 Jul. 18, 2019

Related U.S. Application Data

(63) Continuation of application No. 16/024,335, filed on Jun. 29, 2018, now abandoned, which is a continuation of application No. 14/337,940, filed on Jul. 22, 2014, now abandoned.

(60) Provisional application No. 61/856,828, filed on Jul. 22, 2013.

(51) Int. Cl.
| | |
|---|---|
| *G01N 31/00* | (2006.01) |
| *G01N 33/53* | (2006.01) |
| *G01N 33/50* | (2006.01) |
| *G01N 15/14* | (2006.01) |
| *C12N 5/076* | (2010.01) |
| *G01N 15/10* | (2006.01) |

(52) U.S. Cl.
CPC ......... *G01N 33/5091* (2013.01); *C12N 5/061* (2013.01); *G01N 15/147* (2013.01); *G01N 15/1475* (2013.01); *G01N 2015/1006* (2013.01); *G01N 2015/1472* (2013.01); *G01N 2015/1497* (2013.01); *G01N 2800/367* (2013.01)

(58) Field of Classification Search
None
See application file for complete search history.

(56) References Cited

PUBLICATIONS

Hossainetal. (Asian Journal ofAndrology (2011) 13,406-419).*
Zuckeretal. (Cytometry, vol. 13, pp. 39-47, 1992).*
Johnson etal. (Cytometry, vol. 7, pp. 268-273, 1986).*
Parrish etal. (21st Meeting of the national Association of Animal Breeders, pp. 19-26, 2006).*
Basiji etal. (Clin Lab Med. Sep. 2007; 27(3): 653-viii).*
Parrish JJ, Ostermeier. "Fourier harmonic analysis of sperm morphology," 17th Meeting of the National Association of Animal Breeders, Columbia Mo. pp. 25-31 (1998).
Parrish JJ, Enwall L, Kaya A, Pawshe C, Siddiqui MA, Shamusuddin M. "Sperm Shape Research: An Update," 21st Meeting of the National Association of Animal Breeders, Columbia MO. pp. 19-26 (2006).
Eid LN, Lorton SP, Parrish JJ, "Paternal influence of S-phase in the first cell cycle of the bovine embryo." Biol. Reprod. 1994.51:1232-1237.
Parrish JJ, Eid L. "In vitro fertilization and its relationship to bull fertility." 1994, 15th Meeting of the National Association of Animal Breeders, Columbia MO. pp. 68-73.
Parrish JJ, Schindler J, Willenburg K, Enwall L, Kaya A. "Quantitative sperm shape analysis: What can this tell us about male fertility." 2012. 24th Meeting of the National Association of Animal Breeders, Columbia MO. (in Press).
Zwald NR, Weigel KA, Chang YM, Welper RD, Clay JS. "Genetic selection for health traits using producer-recorded data. II. Genetic correlations, disease probabilities, and relationships with existing traits." Journal of dairy science 2004a, 87:4295-4302.
Zwald NR, Weigel KA, Chang YM, Welper RD, Clay JS. "Genetic selection for health traits using producer-recorded data. I. Incidence rates, heritability estimates, and sire breeding values." Journal of dairy science 2004b, 87:4287-4294.
Peddinti D, Nanduri B, Kaya A, Feugang JM, Burgess SC, Memili E. "Comprehensive proteomic analysis of bovine spermatozoa of varying fertility rates and identification of biomarkers associated with fertility." BMC Syst Biol. Feb. 22, 2008;2:19, 1-13. doi: 10.1186/1752-0509-2-19.m.
Flowers WL. "Management of boars for efficient semen production." J. Reprod. Fertil. Suppl. 1997, 52:67-78.
Gibbs KM, Schindler JR, Parrish JJ. "Determining the effect of scrotal insulation on sperm production in the boar." J. Anim. Sci. E-suppl. 2013, 91:591.
Haralick RM, Shanmugam K, Dinstein I. "Textural features for image classification," IEEE Trans SMC 3. 1973, 610-621.
Parrish JJ. "Bovine in vitro fertilization: In vitro oocyte maturation and sperm capacitation with heparin." Theriogenology 2014, 81:67-73.
Basiji et al., "Cellular Image Analysis and Imaging by Flow Cytometry," Clin Lab Med. 27(3): 653-viii, pp. 1-16 (Sep. 2007).
Hossain et al., "Flow Cytometry for the Assessment of Animal Sperm Integrity and Functionality: State of the Art," Asian Journal of Andrology, vol. 13, pp. 406-419 (2011).
Johnson et al., "Modification of a Laser-Based Flow Cytometer for High-Resolution DNA Analysis of Mammalian Spermatozoa," Cytometry, vol. 7 pp. 268-273 (1986).
Zucker et al., "Utility of Light Scatter in the Morphological Analysis of Sperm," Cytometry, vol. 13 pp. 39-47 (1992).

* cited by examiner

*Primary Examiner* — Lisa V Cook
(74) *Attorney, Agent, or Firm* — Joseph T. Leone, Esq.; DeWitt LLP

(57) ABSTRACT

A method for evaluating sperm fertility. The method includes the steps of obtaining a sample of sperm from an animal of a species; staining the sample with a fluorescent DNA-binding dye; collecting at least one image of the stained sample; determining an edge of a nucleus of at least one sperm within the stained sample in the at least one image; measuring an intensity of the DNA-binding dye within an area defined by the edge of the nucleus of the at least one sperm; determining an average intensity per unit area of the area defined by the edge of the nucleus of the at least one sperm; comparing the average intensity per unit area to an average intensity per unit area for high-fertility sperm and low-fertility sperm of the same species to determine if the sample has high or low fertility.

10 Claims, 7 Drawing Sheets

PREDICTION OF FERTILITY IN MALES

CROSS-REFERENCE TO RELATED APPLICATIONS

This is a continuation of application Ser. No. 16/024,335, filed Jun. 29, 2018 (now abandoned), which is a continuation of application Ser. No. 14/337,940, filed Jul. 22, 2014 (now abandoned), which claims priority to provisional application Ser. No. 61/856,828, filed Jul. 22, 2013.

BACKGROUND

The present invention relates to sperm fertility and in particular to prediction of fertility from DNA staining.

Semen quality examinations are a central role of the semen-processing laboratory. Many semen quality exams exist to evaluate semen. However these tests are often flawed because they are designed to find higher- rather than lower-fertility males, or the approaches reward extreme values rather than those that pass a minimum threshold (Parrish et al., 1998; 2006). In addition, fertility of bulls used in commercial artificial insemination of dairy cattle is likely most dependent on non-compensable semen traits, i.e. traits that cannot be overcome by increasing the number of sperm inseminated. Many semen quality exams, however, target the evaluation of compensable semen traits such as the percentage of motile, live or acrosome-intact sperm.

Research has been directed to potential non-compensable defects in sperm of lower-fertility bulls that alter events during the first cell cycle of the zygote and result in changes to the timing of cell divisions and success of embryo development (Eid et al., 1994; Parrish and Eid, 1994; Parrish et al., 2006). It has been determined that defects or damage in sperm DNA are responsible for these effects. Since a significant portion of the sperm nucleus consists of DNA, it has been hypothesized that subtle changes in sperm DNA might be reflected in physical properties such as sperm nuclear shape. As a result of research in this area, it has been demonstrated that careful measurements of sperm head morphology can be used to predict fertility (Parrish et al., 1998, 2006, 2012). Nevertheless, there is an ongoing need for additional methods to assess fertility.

SUMMARY

Accordingly, disclosed herein are methods for predicting fertility of sperm samples based on the intensity of DNA staining of the samples, based on the surprising observation that brighter DNA staining of sperm heads has a positive correlation with decreased fertility rates.

In one embodiment, the invention provides a method for evaluating sperm fertility. The method includes the steps of obtaining a sample of sperm from an animal of a species; staining the sample with a fluorescent DNA-binding dye; collecting at least one image of the stained sample; determining an edge of a nucleus of at least one sperm within the stained sample in the at least one image; measuring an intensity of the DNA-binding dye within an area defined by the edge of the nucleus of the at least one sperm; determining an average intensity per unit area of the area defined by the edge of the nucleus of the at least one sperm; comparing the average intensity per unit area to an average intensity per unit area for high-fertility sperm and low-fertility sperm of the same species to determine if the sample has high or low fertility.

In another embodiment, the invention provides a method for evaluating sperm fertility. The method includes the steps of obtaining a sample of sperm from an animal of a species, staining the sample with a fluorescent DNA-binding dye, obtaining fluorescent intensity measurements from a plurality of sperm in the stained sample, determining an average intensity of the fluorescent intensity measurements obtained from the plurality of sperm in the stained sample, and comparing the average intensity to average intensities for high-fertility sperm and low-fertility sperm of the same species to determine if the sample has high or low fertility.

DETAILED DESCRIPTION

Figure 1:
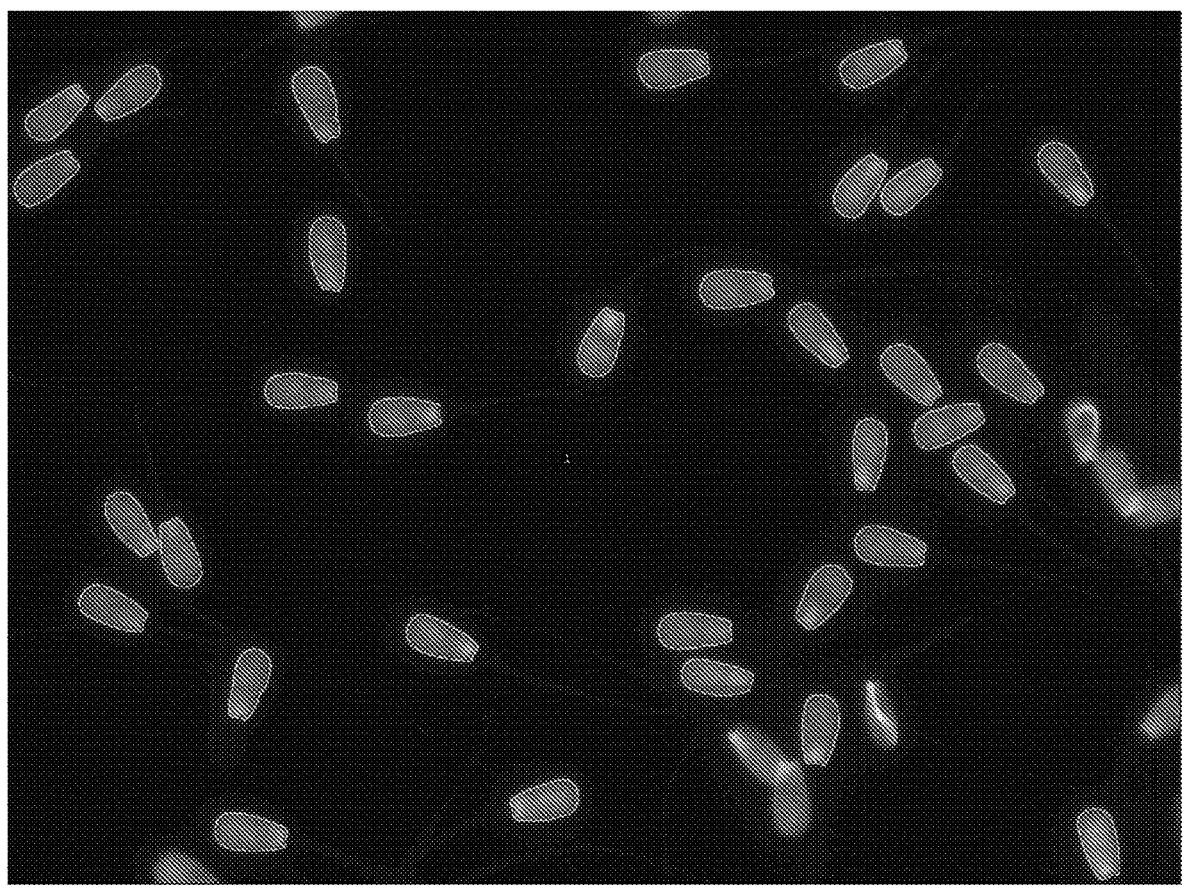
FIG. 1 shows a fluorescent image of bovine sperm stained with HOECHST® 33342(systematic name: 2'-(4-ethoxyphenyl)-5-(4-methyl-1-piperazinyl)-2,5'-bi-1H-benzimidazole) with a line surrounding most of the sperm heads showing the results of the automated edge detection procedure that was used to obtain the outline of the sperm nucleus. Sperm nuclei that touch another sperm, the edge of the image or have a significant distortion were deleted from the analysis and do not have an outline around the sperm nucleus.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Fertility of males is critical to success of animal agriculture as efficient production of the next generation is the single biggest factor to profit or loss. In humans, predicting fertility is important for selecting appropriate assisted reproductive technology of infertile couples. In the pet industry, including dogs and stallions, the high cost of a single insemination dose creates a desire to select males with good fertility or to eliminate purchase of poor fertility males. Semen quality examinations include the collection of methods that a semen-processing laboratory uses to ensure that high quality and fertile semen is shipped to customers whether this is livestock, humans, or pets. Many semen quality exams exist to evaluate semen but few target defects in sperm that would be associated with non-compensable semen defects. We have discovered that low fertility bull sperm or boar sperm suffering summer infertility have increased fluorescence of the sperm nuclei when exposed to a DNA-binding and fluorescent dye such as HOECHST® 33342.

The invention relates to sperm fertility and in particular to prediction of fertility from DNA staining. The method relates to the observation that increased DNA staining of sperm relates to decreased fertility. This provides a relatively straightforward method for assessing fertility of sperm samples that can be used, among other things, by commercial animal breeding facilities to improve success of artificial insemination. The method also detects seasonal infertility when increased DNA staining exists.

As disclosed herein, the methodology includes the steps of obtaining a sample of sperm from an individual of a species; staining the sample with a fluorescent DNA-binding dye; collecting images of the stained sample; determining an edge of the each sperm's nucleus; measuring an intensity of the DNA-binding dye within the sperm nucleus; determining an average intensity per unit area; comparing the average intensity per unit area to an average intensity per unit area for high-fertility and low-fertility sperm of the same species to determine if the sample has high or low fertility. To detect changes due to seasonal infertility the sample is compared to semen collected before or during the periods of seasonal infertility.

In the process of analyzing bull and boar sperm having varying levels of fertility (e.g. due to male to male variation and seasonal variations as well as due to heat stress) it was observed that samples with lower fertility have brighter DNA staining compared to samples with higher fertility, providing a relatively straightforward method for assessing fertility of sperm samples that can be used, among other things, by commercial animal breeding facilities to improve success rates of artificial insemination.

In various embodiments, a fresh or frozen sperm sample is exposed to a DNA-binding fluorescent dye (e.g. HOECHST® 33342), attached to a slide, and imaged using a fluorescence microscope. The fluorescence per unit area of the sperm head is determined and averaged together with like measurements obtained from the same sample. The average sperm head DNA brightness values are then compared between different samples, where the samples may be obtained from different animals and/or from the same animal on different occasions. The samples are then placed into groups based on whether they are low- or high-fertility samples and the average brightness values for the samples from each group are averaged together.

The results of this procedure can then be used to predict whether an unknown sperm sample will have low or high fertility based on whether the average sperm head brightness of the unknown sample is closer to the average brightness for the low-fertility or the high-fertility samples.

The sperm head often has an oval shape which in some species is slightly flattened. Therefore, in order to standardize the fluorescence measurements, in various embodiments sperm heads are selected for imaging and quantitative analysis based on sperm that lay flat on the slide. Sperm which are not flat may have variations in fluorescent intensity due to their particular orientation to the light beam in the microscope.

Figure 2:
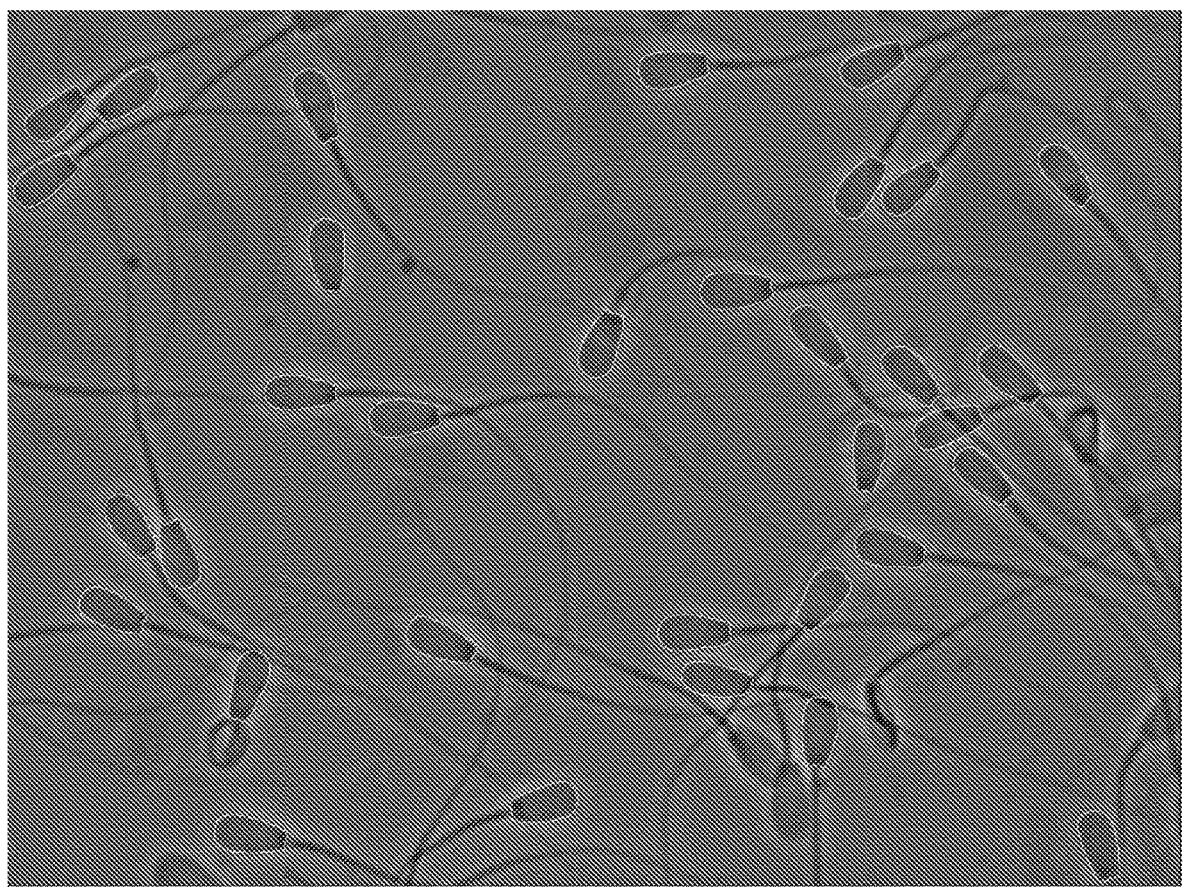
FIG. 2 shows a phase contrast image of the bovine sperm shown in FIG. 1, where the outline of the sperm nucleus was obtained from the HOECHST® 33342 fluorescent image and transferred to this image.

The fluorescence signal of the selected sperm heads is then determined on a per unit area basis, for example per pixel or per square micrometer. The location of the edge of the sperm head cannot always be determined with complete certainty. However, where the edge of the head is drawn can affect the final value of the average brightness of DNA for the head. Therefore, in some embodiments an automated edge-detection scheme is used in order to standardize the determination of the border of the sperm head (FIGS. 1, 2). Even if the automated routine consistently over- or under-estimates the size of the sperm heads, as long as this is consistent across samples the over- or under-estimating effect is expected to cancel out since the results are used for comparison purposes. In one embodiment a series of commands are executed using the NIH ImageJ software package, although other procedures and software packages can be used as well. Other conventional image-processing steps such as background subtraction may also be used provided the steps are used consistently for all samples.

Once the outlines of sperm heads have been determined, the total fluorescence within the outlined area is determined by summing the light intensity of the pixels within the outlined area (taking into account any steps such as background subtraction or other processing steps) and the total intensity is then normalized to a unit area such as per pixel or per square micrometer. For comparison across samples, all of the samples should be normalized to the same unit of area.

While the Examples below pertain to sperm from bulls and boars, it is expected that the procedures are equally applicable to evaluate the fertility of sperm samples from other animals including, without limitation, humans, horses, sheep (ram), and dogs.

Furthermore, while HOECHST® 33342 is used in the Examples below as the DNA-binding fluorescent dye, in various embodiments other DNA dyes could be used. HOECHST® 33342 has been used because it can stain both live and dead sperm, particularly if incubation is at 37-39° C., and has a very high binding affinity and bright fluorescence. In some cases the sperm need to be permeabilized with a detergent (e.g. TRITON® X-100) prior to application or along with the DNA dye to allow the dye to contact the DNA. While HOECHST® 33342 can pass through the lipid membrane, other dyes cannot and therefore need detergent to produce holes in the membrane. Even though the spent' cells are fixed before staining, the paraformaldehyde that is generally used for fixation does not produce large holes in the membrane, at least not reliably. Other fixatives such as ethanol or glutaraldehyde could potentially produce holes in the membrane and be useful approaches to prepare sperm. Such other fixatives are included in this embodiment. There are also other possible dyes including DAPI, YOYO®-1, DRAQ5®, DRAQ7® and propidium iodide, and still other DNA dyes are also possible. Other DNA dyes may be tested with known samples, for example with semen from 10 high- and 10 low-fertility bulls. Semen will be processed as for HOECHST® 33342 except preliminary experiments will establish optimal dye concentration levels and sperm permeability treatments that produce sufficient fluorescence for image analysis. Some of these dyes have higher increases in fluorescence than HOECHST® 33342 when binding to DNA but often have lower binding affinity for the DNA as well. In view of the lower binding affinity, one possible adaptation may be to not remove unbound dye as is done in current procedures with HOECHST® 33342. Thus, optimization of processing conditions for each dye will be investigated. It is predicted that at least some of the DNA dyes listed herein will show an increase in DNA staining intensity that is predictive of infertility as with HOECHST® 33342 staining.

In the bull and boar sperm that are analyzed herein, the nucleus makes up most of the bulk of the sperm head such that DNA staining, which strictly speaking is limited to the nucleus, is an effective measurement of the sperm head. As seen in FIG. 2, the perimeter of each sperm nucleus, each of which is determined based on HOECHST® 33342 staining, matches the outline of the respective sperm head as seen in phase contrast microscopy.

A surprising finding was that the mean intensity of sperm from low fertility bulls was increased along with increased measures of dispersion among the intensity values. At this time it is unclear why the two fertility groups are so different in the various measures of intensity. Without being limited as to theory, this may be due to nuclear condensation during spermatogenesis or the further condensation of nuclei that occurs during passage of sperm through the epididymis.

Calibration of Microscope/Camera System for Fluorescent Intensity Measurements

Given that embodiments of the present invention relies on fluorescent intensity of samples, it is helpful to have a method for standardizing intensity measurements between samples and between data collection systems (including microscopy setups). Quantification of fluorescence via microscopy has an inherent problem in that it is dependent on the fluorescent light intensity delivered to the object (which is based on factors such as the brightness of the light source and the transmission properties of the optical system) and sensitivity of the detecting camera. One factor which may vary even for the same microscopy system is the intensity of the light source, for example a fluorescent bulb's intensity often decreases as the bulb ages; light intensity also varies between microscopes and camera systems.

Thus, utilization of the disclosed methods will be improved in certain embodiments if the implementation also includes steps to standardize conditions (e.g. to obtain consistent lighting on the sample) and/or to adjust/calibrate the resulting data for the particular conditions. To calibrate brightness results so that the results can be more readily compared from one system to another and for the same system over time, calibration curves may be obtained by gathering data from fluorescent standards such as quantum dots or standardized fluorescent microspheres.

Quantum dots or slides containing microsphere standards can be obtained which emit consistent amounts of light in various spectral regions when excited with light having a specific intensity and wavelength. One can quantify how much fluorescence is being produced with this technology and use standard curves to adjust sperm fluorescence intensity on any collection system (e.g. fluorescent microscope setup).

In some embodiments, the calibration data can be used to compare data collected with varying exposure times. On the assumption that the observed light intensity is a linear function of the exposure time, one can alter the exposure times of dots and sperm samples relative to a given set of data collection conditions. If one currently uses a 125 msec exposure time for boar sperm images, this can be increased or decreased by specific amounts and this will deliver proportionally more or less light. For example, doubling exposure will deliver 2× the amount of light and fluorescence intensity. By examining how variation in exposure changes intensity of quantum dots and sperm, one can establish a calibration curve to adjust observed sperm intensity to what a given microscope system delivers using a reference standard such as microspheres or quantum dots and a particular exposure time (e.g. 125 msec). Other exposure settings for other species of sperm can also be calculated using a similar approach.

Thus, in one embodiment, calibration was performed using a slide containing microspheres (MOLECULAR PROBES® ref: F36914 "Focal Check fluorescence microscope test slide #3"; hereinafter referred to as "FCF test slide"; Life Technologies, THERMO FISHER SCIENTIFIC®). The slide contains fluorescent microspheres which emit light at different colors/wavelength ranges. The blue (440 nm emission) microspheres are chosen because their excitation and emission wavelengths are similar to those of HOECHST® 33342, the dye used to obtain fluorescent intensity data on sperm.

The FCF test slide has both bright and dim dot options; the dim dots were chosen and specifically the blue ones were imaged. A series of images were taken on a Nikon Microphot microscope with the setup as described above for either bovine or porcine fluorescent sperm imaging. Images were taken at 250, 500, 625 and 1000 msec exposure times. Images were viewed in Image and dots were thresholded manually using Image tools. The mean intensity of only those spheres that were determined to be in focus in a given image were analyzed. A regression line was then obtained of average intensity (y) vs. exposure time (x) with the intercept going through 0. For one particular set of conditions, the resulting equation will be of the form:

$$y=0.128(x)$$

To calibrate the intensity measurements from a second optical system and compare them to a known system (such as the system described herein) one would image the same fluorescent spheres on the FCF test slide at a range of exposure times using the second optical system and then calculate the equation of a second line that is obtained from the data on the second optical system. One would follow the same protocol used for establishing the standardization line from the known system, including imaging fluorescent microspheres followed by thresholding with ImageJ software and measuring average intensity on only those microspheres that are in focus in a given image.

The equation of the second line will be calculated with the y-intercept also going through 0. The resulting equation will be of the form:

$$y2=m2(x)$$

Next, a calibration coefficient will be calculated by taking a ratio of the slope 0.128 of the original system and the slope m2 determined with the new optical system: c (coefficient) =0.128/m2. All of the intensity values collected on the second imaging system will be multiplied by the coefficient c to allow the intensity values that are obtained on the second system to be compared to the intensity values that would be obtained on the known "standard" system such as that described herein.

Deconvolution

In some embodiments, fluorescence microscopy images of sperm head DNA staining are processed to minimize or remove out of focus information (e.g. out of focus 'blur'), which in one particular embodiment is performed using deconvolution techniques. Deconvolution involves mathematically correcting for the imperfections in an image that arise from the microscopy system. To evaluate the imperfections in the system, an image of a point source of light (e.g. using a microsphere or quantum dot) is collected as a reference to show the distortions caused by the imaging system. The image or collection of images of the dot, which is referred to as a point spread function or PSF, is used in a mathematical deconvolution procedure to undo the distorting effects of the imaging system. In some embodiments a mathematically-determined PSF may be used instead of the images of the microsphere or quantum dot. The deconvolved images of sperm heads are then subjected to further intensity staining analyses as disclosed herein.

Figure 3:
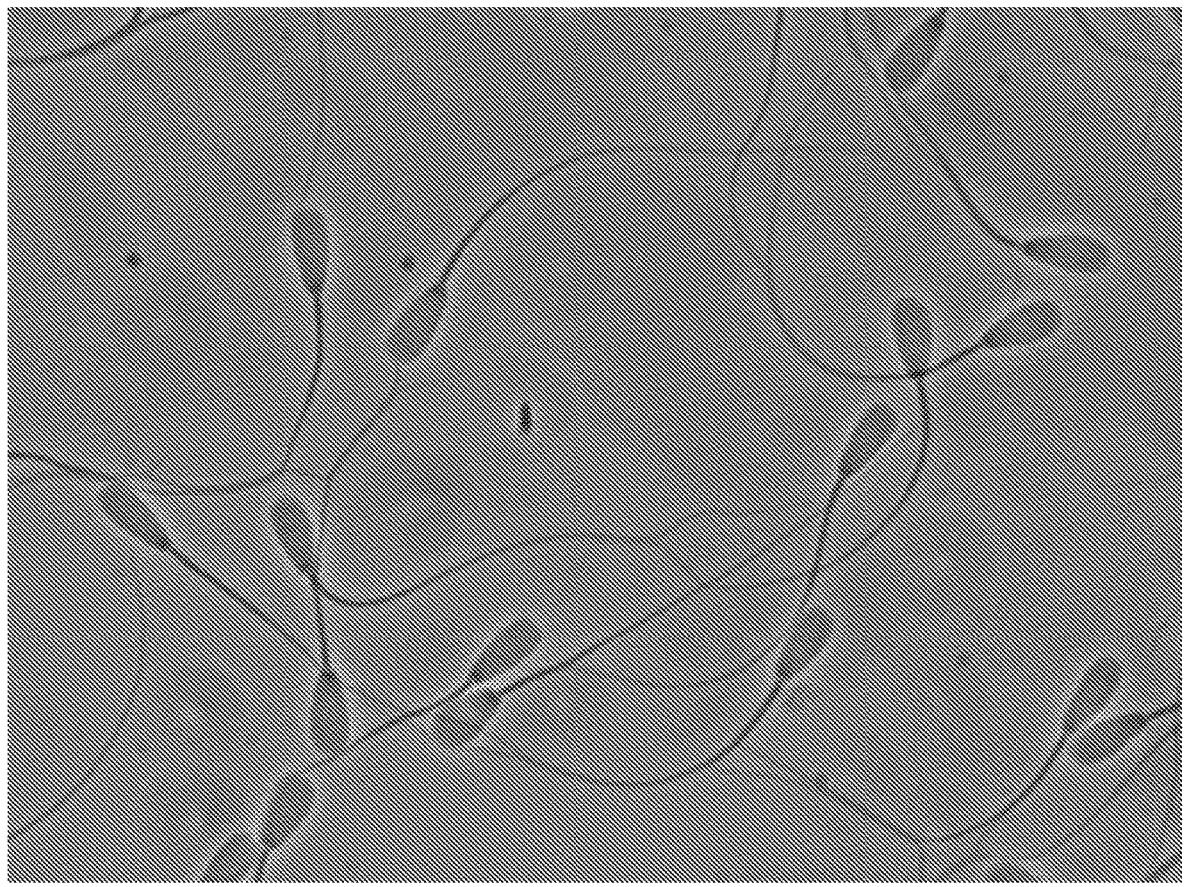
FIG. 3 shows a phase contrast image of bull sperm.
Figure 4:
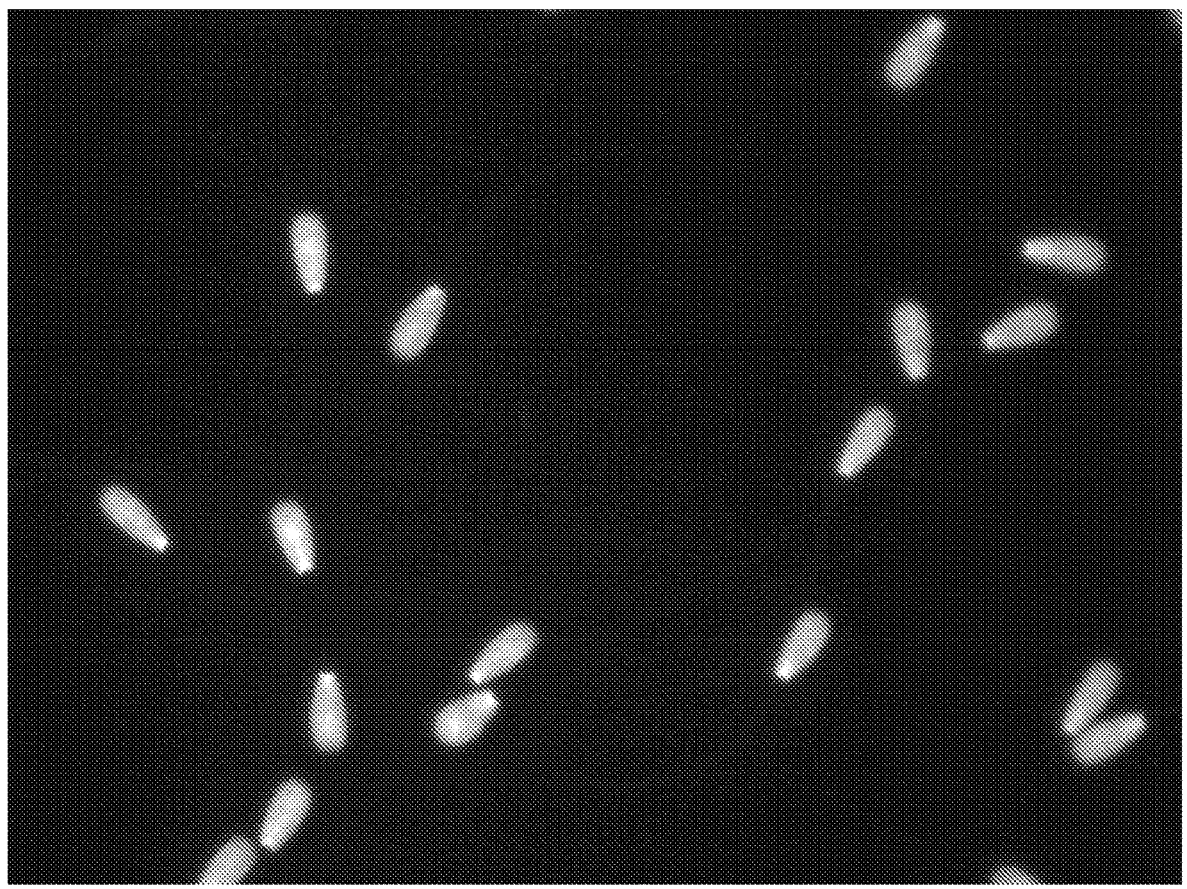
FIG. 4 shows a fluorescent microscope image of HOECHST® 33342 staining for the bull sperm of FIG. 3.
Figure 5:
FIG. 5 shows the sperm heads identified from the images of FIGS. 3 and 4.
Figure 6:
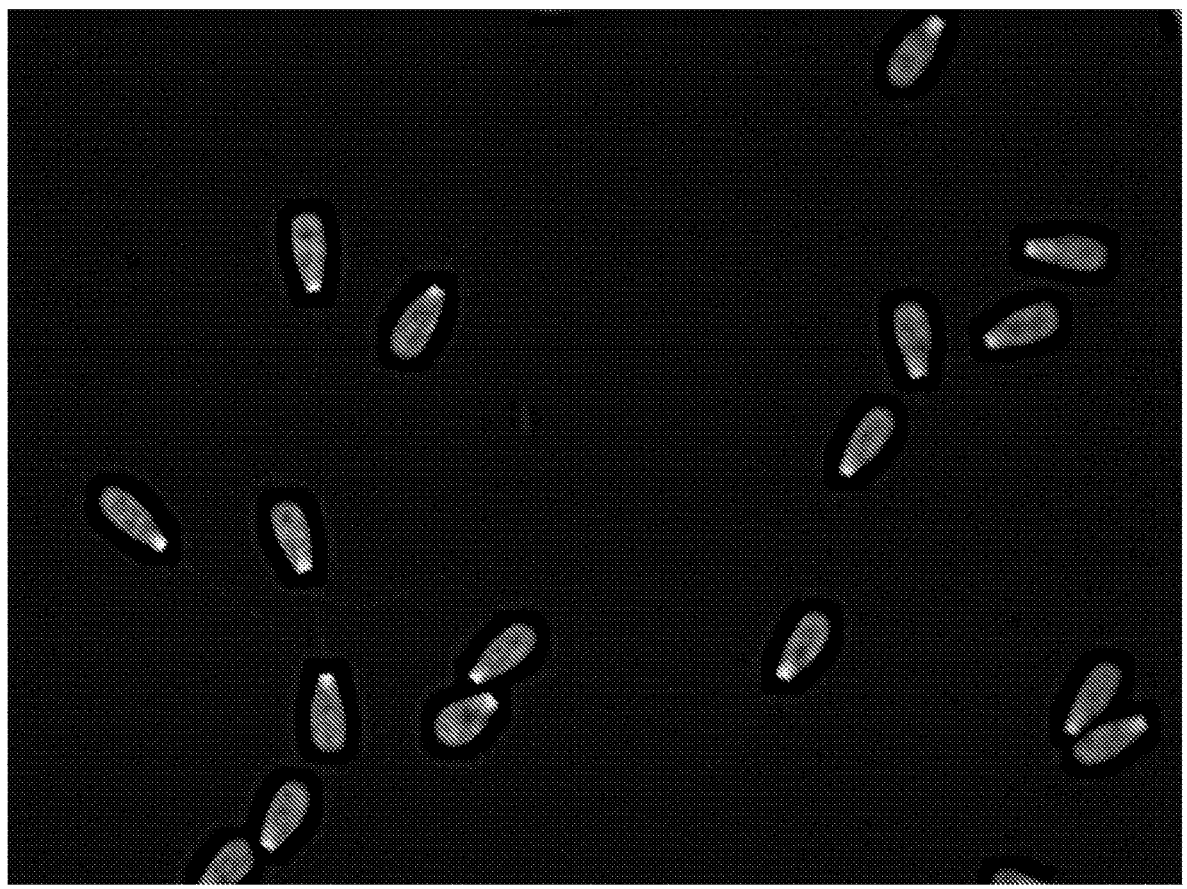
FIG. 6 shows the fluorescently-stained sperm sample of FIG. 4 after deconvolution of the image.

The specific process followed has been to obtain a PSF from an average of 8 quantum dot images. The PS-SPECK™ Microscope Point Source Kit (Molecular Probes® product # P7220) was used to obtain solutions of the quantum dots which are then placed under a cover slip. Images of dots were obtained with ImageJ and 8 dots were averaged. The averaged dot image was then centered on a 1024×1024 pixel image with a black background (although in some embodiments rectangular image sizes also worked). The plugin from ImageJ FIJI release "Parallel Iterative Deconvolution" was used in two dimensions (2d). The approach is to select the HOECHST® image as the blurred image, and then use the square PSF (e.g. 1024×1024 pixels, although other dimensions can be used) as the PSF image, use the Preconditioner as WPL (Weiner Filter), Boundary as Reflexive, Resizing as Auto, Output as Same as source, Precision Type as single, Max number of iterations as 5, Max number of threads as 8. The deconvolved image then has edges of sperm nuclei identified using the same object edges identified in the original HOECHST® image as described above. The intensity measures can now be determined on the deconvolved sperm or various measures of fluorescence (e.g. DNA since the DNA-binding dye HOECHST® 33342 is used to label the sperm) distributions. Additionally, these sperm can be evaluated with the ImageJ "Texture Analyzer" plugin to produce 5 different texture measures, e.g. as defined by Haralick (1973), namely angular second moment, contrast, correlation, inverse difference moment, and entropy. It is important to note that "texture" here refers to the distribution of pixel intensity within an object, in this case a sperm head. Images from the standard intensity analysis (phase, FIG. 3; HOECHST®, FIG. 4; and identified sperm nuclei, FIG. 5) as well as the deconvolution approach (decon) are shown for bull sperm. The deconvolved image has the out of focus fluorescence removed (FIG. 6). Table 1 shows the results from analysis of the 16 sperm identified in FIGS. 3-6. The mean intensity and STD come from the standard analysis on image intensity as disclosed herein. The other measures (texture measures) are derived from the deconvolution analysis. The deconvolution analysis reveals differences from the standard analysis of mean intensity. For example the Contrast value generally increases with increasing mean intensity (see sperm 1 and 2) but sperm 9 has a greater mean intensity than sperm 2 while the contrast of sperm 9 is less than sperm 2. In some embodiments, variations in sperm nuclear texture are expected to be related to male fertility as reflected in one or more of the texture measures shown in Table 1.

TABLE 1

The results of deconvolution analysis for 16 bull sperm also evaluated for mean intensity and standard deviation (STD).

| Sperm | Mean Intensity | STD | Angular Second Moment | Con-trast | Corre-lation | Inverse Difference Moment | En-tropy |
|---|---|---|---|---|---|---|---|
| 1 | 134 | 33 | 0.102 | 25 | 0.00079 | 0.494 | 5.446 |
| 2 | 180 | 45 | 0.030 | 95 | 0.00046 | 0.308 | 6.790 |
| 3 | 133 | 38 | 0.033 | 21 | 0.00078 | 0.426 | 6.278 |
| 4 | 154 | 37 | 0.098 | 44 | 0.00064 | 0.472 | 5.655 |
| 5 | 139 | 33 | 0.033 | 44 | 0.00078 | 0.348 | 6.565 |
| 6 | 128 | 30 | 0.080 | 21 | 0.00087 | 0.481 | 5.653 |
| 7 | 152 | 38 | 0.118 | 41 | 0.00061 | 0.498 | 5.377 |
| 8 | 167 | 40 | 0.128 | 51 | 0.00046 | 0.520 | 5.232 |
| 9 | 188 | 50 | 0.068 | 89 | 0.00040 | 0.384 | 6.224 |
| 10 | 161 | 41 | 0.112 | 53 | 0.00048 | 0.471 | 5.649 |
| 11 | 167 | 44 | 0.118 | 45 | 0.00049 | 0.507 | 5.369 |
| 12 | 132 | 36 | 0.094 | 28 | 0.00085 | 0.464 | 5.613 |
| 13 | 173 | 41 | 0.024 | 85 | 0.00052 | 0.308 | 6.692 |
| 14 | 179 | 43 | 0.081 | 56 | 0.00044 | 0.415 | 6.074 |
| 15 | 142 | 30 | 0.067 | 27 | 0.00072 | 0.433 | 5.996 |
| 16 | 175 | 44 | 0.090 | 61 | 0.00050 | 0.430 | 5.882 |

The following non-limiting Examples are intended to be purely illustrative, and show specific experiments that were carried out in accordance with embodiments of the invention.

EXAMPLES

Example 1

Bull Sperm Fertility and Brightness Determination Procedures

Materials and Methods

Frozen semen samples and fertility data from 107 bulls with varying fertility were provided by ALTA GENETICS® Inc. (Watertown, Wis.). All semen was frozen as per ALTA GENETICS® commercial protocol using egg-yolk Tris extender.

Fertility Prediction and Bull Selection

The fertility data were obtained from ALTA GENETICS® progeny testing. The program consists of more than 180 well-managed dairy farms located in different geographical regions across the United States. Evaluation of fertility of bulls in the program includes DNA verification of paternity and confirmation of pregnancies by rectal palpation or ultrasonographic exam. The outcome of each breeding event was registered into farm management software (DC305, Valley Ag), and the data was collected from partnering farms every three months. The fertility of each bull was predicted using the statistical methods developed by Zwald et al. (2004a,b). The model takes into account the breeding event as well as environmental and herd management factors that influence fertility performance of sires (i.e. effects of herd/year/month, parity, cow, days in milk, sire proven status) as described by Peddinti et al. (2008). Fertility prediction of the sires was expressed as the percentage deviation of its conception rate from the average conception of all bulls. For the present study, 107 bulls with a minimum of 400 breeding records and at least one standard deviation (SD) below or above the average were selected. The respective low- and high-fertility groups thus represented two standard deviations of fertility difference between groups.

Media Required

The following media are required in the preparation of samples: 2.9% Sodium Citrate Buffer (2.9 gm sodium citrate dihydrate, 90 ml distilled water, adjust pH to 7.4, adjust final volume to 100 ml); Hepes buffered saline (0.238 gm Hepes free acid, 0.9 gm NaCl, 90 ml distilled water, adjust pH to 7.4, adjust final volume to 100 ml with distilled water); DABCO mounting media (25 mg 1,4-Diazabicyclo[2.2.2.]octane Triethylenediamine, DABCO, 100 µl Hepes buffered saline, mix until dissolved, 900 µl glycerol, store in dark or foil-wrapped tube); Paraformaldehyde stock solution (4%, 4 gm paraformaldehyde, 50 ml water, mix, add NaOH pellets with mixing until paraformaldehyde dissolves, add 0.238 gm Hepes, adjust pH to 7.4, adjust to 100 ml with water); Parrish citrate fixative (10 ml Paraformaldehyde stock, fill to 100 ml with 2.9% sodium citrate buffer); of HOECHST® 33342 stain solution (5 mg/ml in water made fresh daily).

Slide Preparation

Straws containing sperm samples (0.25 ml or 0.5 ml) were thawed at 37° C. for 60 sec and the contents were expelled into 1.5 ml microcentrifuge tubes. The sperm were diluted 1:1 in 2.9% Sodium Citrate dihydrate solution to a final volume of 500 or 1000 µl respectively. If the volume was 1000 µl, then 500 µl of the diluted sperm sample was placed in a new tube for staining of sperm. The sperm cells were stained by adding 2.5 µl of HOECHST® 33342 stain solution and incubated at 37° C. for 30 min. After incubation, 250 µl of 2.9% Sodium Citrate solution was added to each tube, each of which was then centrifuged at 6,000×g for 15 sec. The supernatant containing excess stain and extender was removed by aspiration. The sperm pellets were resuspended with 650 µl of Parrish citrate fixative and incubated for 3-5 min at room temperature. The fixed samples were briefly vortexed and centrifuged as above, the supernatant removed, and the sperm pellet resuspended with 750 µl of water. The sperm pellet was washed a second time with 750 µl water and centrifuged as above, and then finally resuspended with 500 µl water and vortexed. Then, a 10 µl of sample was placed onto a microscope slide and gently spread out to make homogenous sperm distribution, and allowed to air dry completely on a slide warmer at 37-39° C. Next, a 3.5 µl drop of the DABCO mounting solution was placed on top of the sample to prevent fluorescent fading. An 18×18 mm coverslip was added on top and the edges were sealed with clear fingernail polish.

The procedures for using fresh bovine sperm are the same as for frozen-thawed semen as described above except for sperm dilution to start. Sperm are diluted to either an insemination dose or $40 \times 10^6$ sperm/ml in citrate buffer with BSA (Fraction V BSA at 3 mg/ml in standard citrate buffer). Semen can also be diluted with egg yolk- or milk-based extenders, instead of BSA and then processed as described for frozen-thawed semen citrate buffer.

Image Collection

Sperm cells were imaged on a Nikon Microphot with phase contrast and epifluorescent microscopy (excitation 365±20 nm, dichromatic mirror 400 nm, emission >400 nm); images were collected using a 40× objective, 1.25× magnifier. A QIClick monochrome camera operating in 8 bit mode and using an exposure setting of 62.5 msec was used to collect a tiff format image that was then saved for further image analysis.

Image Analysis Procedures for Bovine Sperm

Images were analyzed with NIH ImageJ version 1.47 m using custom macros to implement the procedures described below. The following describes how an image pair is analyzed, where the image pair includes a phase (p) image and a of HOECHST® 33342 (h) intensity image.

1. Thresholding is applied to the HOECHST® image and sperm nuclear object identified.
    a. Duplicate the image and rename it (e.g. 'h-1').
    b. Apply 'Unsharp Mask' with radius=20 and mask=0.60 to duplicate image.
    c. Apply 'Autothreshold' to the duplicate image selecting the 'IsoData' method with the 'Dark background' box checked.
    d. Apply 'Convert to Mask', followed by 'Dilate,' followed by 'Erode.'
    e. Use 'Analyze Particles' with the following settings: size=700-4500; circularity=0.5-1.0; show=Masks; and with the 'Exclude . . . ,' 'Clear . . . ,' and 'Add . . . ' boxes checked.
    f. Rename resulting image (e.g. 'hmask') and run the 'Fill Holes' routine on the resulting image.
    g. Delete any sperm nuclei that do not appear to be thresholded correctly.

Indications that a given sperm nucleus is not thresholded correctly can include holes in the edge of the sperm head, additional area in a part of the sperm head due to overlapping of another sperm head or tail in the image, presence of fluorescent debris, or an object that has a shape not consistent with the sperm head of the species under investigation.

h. Use 'Create Selection' command to make the perimeter of all sperm nuclei in the image from step f ('hmask') an object. Lay this object on the p image to check if objects are the same approximate size and shape of the sperm head in the p image. If any of the objects are not similar between the p and hmask image, then show the 'hmask' file and delete any non-correct sperm nuclei. Rename the 'hmask' image to 'all'.
    i. Save the 'p', 'h', and 'all' images to a subfolder (e.g. called 'mfiles') as separate images (e.g. 2001.tiff, 2002.tiff, 2003.tiff, respectively) and extending the naming convention with more image sets evaluated.

2. Obtaining intensity values and obtaining mean values:
    a. Access the appropriate 'mfiles' folder for a particular sample.
    b. Set 'Measurements' for mean. Additional measures of the intensity of the object (nucleus) and its dispersion can also be selected as shown in Table 2 and include median, standard deviation, skewness, and kurtosis. It is also possible to select other measures that describe the object such as perimeter and ellipse. The perimeter is simply the outside boundary of the selected sperm head. The ellipse option fits an ellipse to the sperm head and the major axis of the ellipse is the length and minor axis the width. The perimeter, length and width may be expressed in µm or other suitable units.
    c. Select the first 'all' image (e.g. 2003.tiff), use 'Analyze Particles' with: size=0-Infinity, circularity=0.00-1.00, show=Nothing, and with the 'Display . . . ', 'Exclude . . . ', 'Include . . . ', and 'Add . . . ' boxes checked.
    d. Data per sperm is saved in a results table.
    e. The next 'all' image (e.g. 2006.tiff) is opened and the above steps are repeated. This continues until no more 'all' images exist. The results are saved and evaluated within Statistical Analysis System (SAS Inc.).
    f. Within SAS, 100 randomly-selected sperm from those evaluated are selected and means from those selected sperm are obtained for the various measurements.

Bull Sperm Measurement Results

This Example involves evaluating sperm from two populations of bulls that represent extremes of fertility, with a difference of 8.8% fertility between the two populations. This is the largest difference that can be obtained on a population of bulls used for commercial insemination. There were 53 bulls in the high fertility group and 54 in the low fertility group. The mean±sem number of breedings used to determine fertility for the high and low fertility groups was 2368±324 and 1124±137, respectively.

Samples were collected and analyzed as described above. Results comparing mean intensity of HOECHST® 33342 staining in the sperm head and other parameters measured on the 'h' image are shown in Table 2. There were differences in mean intensity, standard deviation of intensity, skewness of intensity, kurtosis of intensity, median of intensity, area of the sperm head, perimeter, and width between sperm from the two fertility groups (p<0.05). Surprisingly, the low fertility bulls have an increased intensity and variation between sperm heads. The low fertility bulls also have sperm with a smaller area, perimeter, and width.

TABLE 2

The mean ± SEM for bulls in the two fertility groups for mean intensity (INT, in arbitrary fluorescence units) and other measures of sperm head characteristics determined directly from ImageJ.

| Criteria | Fert1 (high) N = 53 | Fert2 (low) N = 54 | p value (ANOVA)c |
|---|---|---|---|
| Fertlity Group | 4.1 ± 0.1 | −4.7 ± 0.3 | — |
| Mean INT | 99 ± 3 | 109 ± 3 | 0.0078 |
| Std of Mean INT | 19.0 ± 0.6 | 22.2 ± 0.6 | 0.0002 |
| Skewness of INT | 0.0088 ± 0.0316 | 0.1741 ± 0.0278 | 0.0001 |
| Kurtosis of INT | −0.2681 ± 0.0483 | −0.0879 ± 0.0484 | 0.0097 |
| Median of INT | 100 ± 3 | 110 ± 3 | 0.0138 |
| Area (microns) | 31.3 ± 0.2 | 30.4 ± 0.2 | 0.0017 |
| Perimeter (microns) | 23.08 ± 0.07 | 22.79 ± 0.09 | 0.0151 |
| Length (microns) | 8.96 ± 0.03 | 8.85 ± 0.05 | 0.0611 |
| Width (microns) | 4.45 ± 0.02 | 4.37 ± 0.02 | 0.0041 |

Example 2

Sperm Nuclear Structure of Boars is Impacted by the Summer Environment

The experiments in this Example involved the evaluation of boar semen collected over the summer of 2012. During the summer, it is known that boar semen declines in fertility in response to increases in summer temperatures (Flowers, 1997). The summer of 2012 was extreme in Wisconsin with daily high temperatures during the period of our study exceeding 90° F. on 38 days compared to an average of 12 days in a normal year. In Table 3, it can be observed that boar sperm nuclei change in their ability to have their DNA stain with HOECHST® 33342 that includes an increase in mean fluorescent intensity as well as increases in the length and width of the sperm heads.

The data from boars is similar to the bull data, except that the bull sperm data was correlated with known female fertility information. For boars, on the other hand, fertility is inferred from a known seasonal decline in fertility. As shown above, low fertility bulls had high mean fluorescent intensity of their sperm nuclei which is what is demonstrated below to occur to boar sperm nuclei as the period of summer infertility occurred. In contrast to bulls, in which higher fertility sperm have larger heads that those of low fertility groups, boar sperm nuclei increased in length and width during a period in which it is expected that fertility decreases. Low fertility bull sperm decreased in length and width of the heads. This may be due to the differences in geometry of the boar sperm as they are more tubular than bull sperm. The reason for the changes in sperm nuclear parameters of bulls and boars is unclear at the present time. This may be due to nuclear condensation during spermatogenesis or changes to condensation of nuclei that occurs during passage of sperm through the epididymis. The differences in sperm nuclear intensity, length, and width provide the means however to identify bulls of different fertility.

For boar ejaculates, the differences in nuclear intensity, length, and width provide the means to identify a male suffering from summer heat stress and, by correlation with the known decline in fertility over the course of the summer, the means to predict lower fertility.

Materials and Methods

Semen was collected at a commercial boar stud in Southern Wisconsin from Jun. 18, 2012 to Nov. 2, 2012. The number of boars collected each week and the Wednesday date for a particular week are listed in Table 3. The number of boars from which samples were collected/week ranged from 45-60 over the course of the summer of 2012. Boars were only those that were used for single sire insemination. It is known that fertility of boars declines over the course of the summer with peak declines occurring from July-August. Thus the samples represent the period of time when fertility of these specific boars are expected to decline.

Media

The following media are required in the preparation of samples: 2.9% Sodium Citrate Buffer (2.9 gm sodium citrate dihydrate, 90 ml distilled water, adjust pH to 7.4, adjust final volume to 100 ml); Hepes buffered saline (0.238 gm Hepes free acid, 0.9 gm NaCl, 90 ml distilled water, adjust pH to 7.4, adjust final volume to 100 ml with distilled water); DABCO mounting media (25 mg 1,4-Diazabicyclo[2.2.2.] octane Triethylenediamine (DABCO), 100 µl Hepes buffered saline, mix until dissolved, combine with 900 µl glycerol); Paraformaldehyde stock solution (4%; 4 gm paraformaldehyde, 50 ml water, mix, add NaOH pellets with mixing until paraformaldehyde dissolves, add 0.238 gm Hepes, adjust pH to 7.4, adjust to 100 ml with water); Parrish boar citrate fixative (6.25 ml Paraformaldehyde stock, fill to 100 ml with 2.9% sodium citrate buffer, add 300 mg Bovine Serum Albumin, pass through a 0.22 µm filter to sterilize); dye HOECHST® 33342 stain solution (1 mg/ml in water made fresh daily).

Sample and Slide Preparation

Following semen collection, 0.25 ml semen is added to 0.75 ml of the Parrish boar citrate fixative, mixed and shipped to the lab for further analysis. Upon arrival at the lab, fixed semen is stored at 5° C. until further analysis. Concentration of the semen sample in the fixative is determined using a spectrophotometer at 650 nm. To a 1 ml cuvette, add 0.9 ml of the sodium citrate buffer, zero cuvette, add 0.1 ml of the fixed semen sample, measure absorbance. Adjust the sample to 0.2 absorbance, using the Parrish boar citrate fixative. This will yield a sperm concentration approximately $40 \times 10^6$ sperm/ml.

To stain sperm, place 500 µl of the $40 \times 10^6$ sperm/ml semen in a 1.5 ml micro-centrifuge tube, add 2.5 µl of HOECHST® stain, vortex briefly and incubate at 35-37° C. for 30 minutes. Centrifuge the stained sample in microcentrifuge at maximum at 6000 g for 15 seconds. Remove supernatant, vortex for 1-2 seconds, and suspend the sperm pellet in 750 µl of the Parrish boar citrate fixative. Repeat the centrifugation, remove supernatant, suspend with 750 µwater. Place 10 µl of sample on a slide and dry on a stage warmer. When dry, sample can be stored if desired. To continue on, add 3.5 µl of the DABCO mounting media over the sample, add a 18 mm×18 mm, #1 or #1.5 coverslip. After mounting media reaches the edge of coverslip, seal with clear finger nail polish. When the finger nail polish dries, repeat to ensure a complete seal.

Image Analysis

Sperm cells were imaged on a Nikon Microphot with phase contrast and epifluorescent microscopy (excitation 365±20 mu, dichromatic mirror 400 nm, emission >400 nm), using a 40× objective and 1.25× magnifier. A QIClick monochrome camera operating in 8 bit mode and using an exposure setting of 125 msec was used to collect a tiff format image that was then saved for further image analysis.

Images were analyzed with ImageJ 1.47 m using a combination of procedures available within ImageJ and custom designed macros. The following is how an image pair is analyzed. The image pair is a phase (p) image and a HOECHST® (h) image of the same field of view. Thresholding is applied to the HOECHST® image and the sperm nuclear object identified. The main difference from the bull procedure (see above) is the thresholding approach. The 'h' image is duplicated and renamed as 'h-1', it is then smoothed, and laplacian edge detection is done with a smoothing of 3 applied. The resulting image has the contrast enhanced with a saturation=1 and normalization applied. Now an autothreshold of MaxEntropy is applied with threshold remaining dark. The resulting image is dilated and then eroded.

The remaining steps described are the same as for the bull sperm, as discussed above. The analyze particles routine in used with size=700-4500, circularity=0.5-1.0, show=Masks, exclude, clear, and add selected. The resulting image is renamed as 'hmask' and a fill holes routine run. The custom macros next allow the user to delete any sperm nuclei that appear not thresholded correctly. The create selection command is then used to make the perimeter of all sperm nuclei in 'hmask' an object that is then overlaid on the 'p' image to check if objects are correct. If any are not correct, then the user has the option to delete any non-correct sperm nuclei. Lastly the 'hmask' image is renamed to 'all'. The 'p', 'h' and 'all' images are then saved to a subfolder called 'mfiles' as image 2001.tiff, 2002.tiff, 2003.tiff respectively and extending with more image sets evaluated.

To obtain the intensity values as well as the length and width of the sperm heads, in the set measurements dialog box in Image the mean gray value and shape descriptors options should be selected. Now select the first all image (for example, 2003.tiff) use analyze particles command with size=0-Infinity, circularity=0.00-1.00 show=Nothing, display, exclude, include, and add checked. Data per sperm is then saved in a results table. The next all image, 2006.tiff is opened and steps repeated. This continues until no more all images exist. The results are saved as means per sample generated within Statistical Analysis System (SAS Inc.) or can be directly generated within ImageJ using the summarize command. Within SAS it is possible to randomly select 100 sperm from those evaluated and then obtain the means from those selected sperm.

Results

Semen was collected over a 20-week interval in the summer of 2012. Data is presented in Table 3 and is expressed as the mean±SEM among boars collected in a particular week. The listed date for each week corresponds to the Wednesday date for the particular week. The data collected included the mean fluorescent intensity along with the length and width of the sperm nucleus as determined from the fluorescent image of the HOECHST® stained sperm, where the data are presented as mean±sem. Data in each week were compared to the data in the Jun. 20, 2012 week, which was considered the control representing sperm not yet expressing summer heat stress. There were no differences, $p>0.05$, between data in week Jun. 20, 2012 and Jun. 27, 2012 for all 3 measurements. Beginning in week Jul. 4, 2012 and continuing through week Oct. 3, 2012 the mean intensity of sperm nuclei was greater than seen in week Jun. 20, 2012, $p<0.05$. The other measures showed differences as the summer progressed but required longer to return to pre-heat stress measurement levels. Effects of heat stress on boars requires >35 days for recovery (Gibbs et al., 2013). As the last days of >90° F. (heat stress temperatures) occurred during the week of Sep. 5, 2012, it was predicted from the Gibbs et al. (2013) data that recovery of any heat stress effects would occur by the week of Oct. 10, 2012. This is indeed what was observed. Over the course of the summer, there was an increase in the mean intensity, length and width of sperm nuclei.

TABLE 3

Changes in boar sperm nuclear intensity, length and width over the summer of 2012. Dates indicate the Wednesday date for each specific week. Values shown are mean ± sem and ANOVA was used for analysis.

| Date | Boars (#) | Intensity | Length (µm) | Width (µm) |
| --- | --- | --- | --- | --- |
| Jun. 20, 2012 | 45 | 104 ± 5 | 8.49 ± 0.04 | 4.16 ± 0.02 |
| Jun. 27, 2012 | 46 | 106 ± 4 | 8.48 ± 0.03 | 4.15 ± 0.02 |
| Jul. 4, 2012 | 53 | 115 ± 2* | 8.50 ± 0.03 | 4.23 ± 0.01* |
| Jul. 11, 2012 | 53 | 122 ± 3* | 8.55 ± 0.03 | 4.24 ± 0.01* |
| Jul. 18, 2012 | 48 | 137 ± 2* | 8.53 ± 0.03 | 4.19 ± 0.01 |
| Jul. 25, 2012 | 50 | 147 ± 3* | 8.59 ± 0.04 | 4.24 ± 0.01* |
| Aug. 1, 2012 | 50 | 143 ± 2* | 8.64 ± 0.03* | 4.27 ± 0.01* |
| Aug. 9, 2012 | 52 | 148 ± 2* | 8.58 ± 0.04 | 4.24 ± 0.01* |
| Aug. 15, 2012 | 52 | 158 ± 2* | 8.66 ± 0.03* | 4.22 ± 0.01* |
| Aug. 22, 2012 | 49 | 128 ± 2* | 8.66 ± 0.04* | 4.23 ± 0.01* |
| Aug. 29, 2012 | 60 | 139 ± 2* | 8.71 ± 0.03* | 4.26 ± 0.01* |
| Sep. 5, 2012 | 54 | 145 ± 3* | 8.73 ± 0.03* | 4.27 ± 0.01* |
| Sep. 12, 2012 | 56 | 141 ± 3* | 8.72 ± 0.03* | 4.25 ± 0.02* |
| Sep. 19, 2012 | 52 | 150 ± 3* | 8.70 ± 0.03* | 4.22 ± 0.02* |
| Sep. 26, 2012 | 55 | 144 ± 3* | 8.71 ± 0.03* | 4.24 ± 0.01* |
| Oct. 3, 2012 | 55 | 115 ± 2* | 8.69 ± 0.02* | 4.26 ± 0.01* |
| Oct. 10, 2012 | 56 | 98 ± 2 | 8.71 ± 0.02* | 4.23 ± 0.01* |
| Oct. 17, 2012 | 50 | 93 ± 3 | 8.68 ± 0.03* | 4.25 ± 0.01* |
| Oct. 24, 2012 | 56 | 111 ± 3 | 8.68 ± 0.03* | 4.21 ± 0.01 |
| Oct. 31, 2012 | 46 | 106 ± 3 | 8.62 ± 0.03 | 4.19 ± 0.01 |

A * indicates a difference greater than date Jun. 20, 2012, $p < 0.05$.

Example 2a

Analysis of Sperm DNA Staining Intensity in Boars During Non-Heat Stress Periods In some embodiments, additional studies will be performed to determine if there is a correlation between sperm head DNA staining intensity in boars during non-heat stress periods. It is predicted that the correlation between higher intensity and decreased fertility that has been seen in heat-stressed boars as well as with non-heat stress bulls will also be seen in non-heat stress boar samples.

The time interval for seasonal fertility differences is different for males and females. Females exhibit reduced fertility±2 weeks from a heat event while boars ejaculate defective sperm 21-35 days following the heat event. The last significant heat events of the summer of 2012 occurred during August based on available temperature records. The comparison of earlier data (e.g. from September) and later collected data (e.g. from October and November) thus provides the ability to remove the sow effect in comparisons. Thus, semen and fertility records from October-November 2012 may be used and then compared to data for October-November of 2013 to compare boar fertility and fluorescent intensity of sperm nuclei in a period of the year with no summer infertility effects present for either the sow or boar. Boars will be grouped as either being of high or low fertility and then sperm fluorescent intensity will be compared between these two groups. This will allow a similar comparison as was done for bulls of differing fertility. Fertility data will include farrowing rate (conception data) and pigs/litter born for matings to these boars. In various embodiments, data will be collected from at least 50 matings to provide statistical significance. Accordingly, semen and records from 2012 and 2013 will be used to ensure there is sufficient data from boars to perform meaningful statistical comparisons.

Example 3

Human Sperm Samples

In this Example, the relationship of sperm evaluation using Fourier Harmonic Amplitudes (FHA; see Parrish et al. 2006) and DNA staining intensity of human sperm to fertility measure by TI, IUI and IVF (with or without intracytoplasmic sperm injection, IVF±ICSI) will be studied. Sperm nuclear shapes will be described using FHA in a population of normal and infertile males from couples seeking fertility treatment. In addition, canonical discriminant analysis will be used to determine if FHA variables are able to predict fertility of sperm samples as indicated by pregnancy outcome following fertility treatment (TI, IUI, or IVF±ICSI). Further, DNA staining intensity will be described in a population of normal and infertile males from couples seeking fertility treatment. Finally, DNA staining intensity will be predictive of male fertility treatment outcomes as indicated by pregnancy outcome following fertility treatment (TI, IUI, or IVF±ICSI).

It is estimated that of the 15% of human couples that are infertile, half of those couples suffer from male infertility and more than 50% of those men have idiopathic infertility. Male subfertility or infertility also plays an important part in the decrease in reproductive efficiency of agricultural species (cattle, swine, sheep, horses). Predicting male fertility from semen characteristics is important in both domestic animals and humans. Diagnosis of male factor infertility is often based on "abnormal" semen analysis even though it sometimes fails to accurately predict a man's fertility. Therefore, there has been a search for other tests to improve the evaluation of infertile males. Treatment of idiopathic "unexplained" infertility consists of ovulation induction with timed intercourse (OI/TI) and intrauterine insemination (IUI), which has pregnancy success rates of approximately 4-8% per cycle respectively. The pregnancy rate increases to over 50% with in vitro fertilization (IVF) in patients younger than 35. Current semen analysis criteria however do not discriminate between patients who will benefit from IUI and those that need IVF. This highlights the shortcoming of current fertility evaluation, in particular SA.

Fertility in the male is a complex trait that can be impacted by both compensable and non-compensable components. Reduced fertility caused by compensable components, such as sperm numbers, motility, morphology, and ability to undergo capacitation and acrosome reaction, can be overcome by increasing the number of sperm inseminated. Non-compensable components include traits associated with binding of sperm to the oocyte plasma membrane, DNA integrity, and genetic mutations. These traits are those that impact the ability of the embryo or zygote to develop after oocyte activation by the sperm. They pose a dilemma because these traits are hard to evaluate and there are currently limited solutions (Assisted Reproductive Technology) for increasing fertility if these traits are found. A number of tests routinely used for semen evaluation describe the compensable defects, however they lack the ability to identify the non-compensable defects that result in reduced fertility. In cattle, semen from different bulls, which meet minimum quality requirements, can differ in fertility by 20-40%. The same is true for the clinical value of WHO criteria for basic semen analysis (concentration, morphology and motility) in the prediction of fecundity. Tests for non-compensable traits have been developed and include hamster zona-free ovum test (HZFO), sperm chromatin structure assay (SCSA) and a myriad of genetic tests. However, a simple, objective test that could be incorporated routinely in semen analysis in the clinic, and that is highly correlated with fertility has yet to be identified.

Sperm cells are unique in that DNA accounts for 90% of the total nuclear volume, is highly organized and condensed, and transcriptionally inactive. Any aberration in the nuclear matrix or chromatin packaging should result in a change in sperm nuclear shape, although it would be minute. FHA is a procedure that uses quantitative binding of fluorochromes HOECHST® 33342) to sperm nuclear DNA as a method to accurately describe the curvature of the perimeter of the sperm nucleus with computer aided image analysis. Changes in the sperm nuclear shape determined with the FHA method are not visible with the naked eye but are correlated with male fertility in the species tested (bull, boar). Comparison of FHA to SCSA shows that although the two tests are related, FHA is able to describe alteration in chromatin structure within specific regions of the nucleus that are critical to fertility. While FHA is a powerful technique for evaluating sperm properties, there is a need for other evaluation techniques which may complement FHA or which may be used alone, particularly other techniques which may be more straightforward to use in practice such as intensity-based techniques.

As disclosed herein, it is possible to measure the average intensity of fluorescence in sperm nuclei from a particular male. The average fluorescence intensity correlates with bull and boar fertility as disclosed herein. Bovine embryos produced by in vitro fertilization (IVF) from bulls of lower fertility divide later to two cells and have fewer cells at the blastocyst stage. Sperm from bulls challenged with a heat event either experimentally induced with testicular insulation for 48 hours, or from summer heat stress in Wisconsin, have sperm with specific FHA profiles linked to lower fertility in previous studies and also have IVF results similar to lower fertility bulls. Analysis of sperm nuclear morphology with FHA and DNA staining intensity, as disclosed herein, shows that both correlate with fertility in bulls and boars. Accordingly, these results will be extended to human samples.

Human semen samples will be obtained from discarded sperm from semen anlaysis, IUI, or IVF±ICSI from men with partners undergoing fertility investigation (SA), or fertility treatment (IUI or IVF±ICSI). Samples may be obtained from up to 250 men (with or without their partners, 250 adult women), 18 years old or older who are partners in couples diagnosed with infertility. All male partners of couples will be routinely evaluated with semen analysis to diagnose male factor infertility. The samples will be processed per standard laboratory procedures for semen analysis and treatments with IUI or IVF±ICSI. Sperm samples used for semen analysis, or IVF±ICSI will be materials that are either donated (if consent was given by the patient) or discarded per standard operating procedures. Only after the sperm necessary for the clinical semen analysis, IUI, or IVF±ICSI are removed will the sample for research be obtained from the unused liquefied or processed sample. All donated excess sperm samples will be diluted 1:3 into tubes of fixative (2.9% NaCitrate, 1.0% paraformaldehyde, 3 mg/ml BSA). The fixative will render the sperm non-viable and preserved for nuclear morphology and DNA staining analysis. No more than 2.0 ml of semen will be required (usually containing 10-40×10$^6$ sperm). Tubes will be labeled with the IRB protocol number, identification of contents (3.0 mL 1% paraformaldehyde), and serial study number. If the patient initiates a pregnancy, a link between the sample data and the medical record number will be maintained for 9 months to ascertain pregnancy outcomes in couples whose partners have consented to the study.

While sperm may be collected from up to 250 males, based on data gathered from sperm of other species as few as 10 samples in both the normal and lower fertility populations may be required to determine a statistical difference in FHA. To correlate FHA criteria in humans and in relation to pregnancy outcome in different fertility treatment groups however, it may be necessary to collect data on a larger sample size since no there is no existing data on FHA in humans and/or on FHA and pregnancy outcomes in humans. It is presently unclear as to the means and variance in the population, which may not be the same as in domestic animal populations, which are somewhat selected for fertility. Thus, in one embodiment 100 samples will be collected from subjects undergoing semen analysis and 50 samples from each of the treatment arms (IUI, IVF, ICSI), for a total of 250 patients.

Experimental Analysis

Data will be collected from image analysis of fluorescently stained sperm dried onto slides or evaluated through flow cytometery. The perimeter coordinates are converted in Statistical Analysis Systems (SAS) software to Fourier functions and then harmonic amplitudes of the functions determined. Discriminate analysis will be used to determine the best method to separate the fertile and subfertile/infertile males based on nuclear shape, nuclear staining, sperm laboratory tests, and measures of TI, IUI, IVF±ICSI success. Diagnostic statistics will be used to determine the best discriminate model for predicting the fertility potential of a particular male.

Sample Preparation

Aliquots of the fixed sample will be stained with HOECHST® 33342, with excess stain removed by centrifugation and the sperm pellet resuspended in water. The stained sample will be dried onto microscope slides, antifade agent used to mount a coverslip, and sealed with fingernail polish to preserve the sample for imaging. This procedure has been used successfully for imaging sperm from multiple species (bull, boar, stallion, dog). The slides will be imaged with phase contrast and epifluorescent microscopy as disclosed herein. The images will be evaluated using a specifically written ImageJ-based program for sperm head morphology (phase contrast, epifluorescence), sperm head perimeter output (used for FHA analysis), mean and variation in sperm head fluorescent staining intensity (epifluorescence), sperm head shape parameters to include area, length, width, perimeter, aspect ratio, roundness and solidity, and nuclear texture measures of angular second moment, contrast, correlation, inverse difference moment, and entropy following deconvolution analysis . A second aliquot of semen will be stained with the same procedure but evaluated for fluorescence intensity with flow cytometry. Remaining samples will be stored refrigerated in a locked room. Suitable procedures will be followed throughout to maintain patient confidentiality.

It is expected that the correlation between increased DNA staining intensity and decreased fertility that has been seen in other species (e.g. bull and boar) will also be observed in human samples. It is also expected that results of DNA staining intensity will correlate with the results of FHA analysis and that both analysis methods will be predictive of fertility. It is further expected that the deconvolution of sperm DNA will produce measures of DNA distribution within sperm nuclei that are predictive of fertility. The approaches are also expected to produce methods to evaluate if sperm are suitable for IUI or ICSI.

Example 4

Sperm Intensity Measurements Using Flow Cytometry

While other embodiments disclosed herein utilize fluorescent microscopy of a sperm attached to a substrate such as a glass slide, in some embodiments sperm DNA intensity staining will be evaluated using flow cytometry. Most sperm are flat and paddle shaped, which is the case for several of the species discussed herein. By attaching paddle-shaped sperm to a slide, sperm heads tend to be imaged perpendicular to that flat surface. Given this orientation this is likely the lowest fluorescent intensity obtainable, while changing sperm orientation relative to the fluorescent light beam would mean the light would pass a greater amount of the DNA and would produce increased fluorescence intensity.

An alternative technology to measuring fluorescence with a microscopy system is flow cytometry. However, as sperm pass through the sheath fluid of a flow cytometry system, the sperm heads are randomly oriented but with the head pointing forward. Due to this random orientation of sperm heads there tend to be varying amounts of fluorescence emitted from the heads, depending on what proportion of the sperm head DNA is exposed to the light beam. Nonetheless, using a flow cytometer one can take measurements on 20,000 sperm or more as compared to 100-200 sperm with fluorescence microscopy and manual image analysis. In some embodiments, orientation-dependent DNA staining intensity measurements from flow cytometry may average out if a large enough population of sperm are measured. To determine the extent to which this is true, one set of experiments will be directed to measuring and comparing both microscope-derived and flow cytometer-derived fluorescence intensity for the same semen samples. In some embodiments, a sorting flow cytometer will be used which includes an orienting nozzle for sperm heads so that the intensity measurements are obtained when each sperm head is in approximately the same orientation in order to even out variation due to the angle at which the excitation beam strikes the sperm head. In various embodiments, sperm samples from a number of different species will be evaluated using flow cytometry, including bull, boar, human, dog, stallion, and other species including those listed herein.

Given the complexity of flow cytometry output (e.g. which can include graphs of 1- and 2-dimensional data with peaks in various locations on the graphs), additional studies will be performed to determine how to interpret the flow cytometry results. For example, studies will be performed to identify which peaks are best at predicting whether the sperm is fertile or infertile. In some embodiments (particularly when sperm heads travel through the flow cytometer in random orientations), there may be several peaks of intensity seen on the flow cytometry data graphs; therefore, additional studies will be performed to determine which peak(s) are predictive of fertility/infertility (or ratios of peaks, or threshold peak levels, etc.).

Flow cytometer experiments were conducted using the same bull sperm samples as were used to obtain the data listed in Table 2. Straws containing sperm samples (0.25 ml or 0.5 ml) were thawed at 37° C. for 60 sec and the contents were expelled into 1.5 ml microcentrifuge tubes. The sperm were diluted 1:1 in 2.9% Sodium Citrate dihydrate solution to a final volume of 500 or 1000 µl. If the volume was 1000 µl, then 500 µl was placed in a new tube for staining of sperm. The sperm cells were then stained by adding 2.5 µl of HOECHST® 33342 stain solution and incubated at 37° C. for 30 min. The sample was next split, with half (250 µl) remaining in the stain solution termed unwashed and the other half (250 µl) processed to remove non-bound stain. To remove excess non-bound stain, the 250 µl sperm sample was mixed with 500 µl of the Parrish Fixative solution and centrifuged at 6,000×g for 15 sec. The sperm pellet was then mixed with 750 µl of Parrish Fixative solution, centrifuged at 6,000×g for 15 sec, sperm pellet resuspended with 750 µl of Dulbecco's PBS (No $Ca^{2+}$ or $Mg^{2+}$), centrifuged at 6,000×g for 15 sec, and the sperm pellet resuspended with 150 µl of Dulbecco's PBS. The sample was then transported to a 5 laser BD LSRII flow cytometer for analysis.

Figure 7:
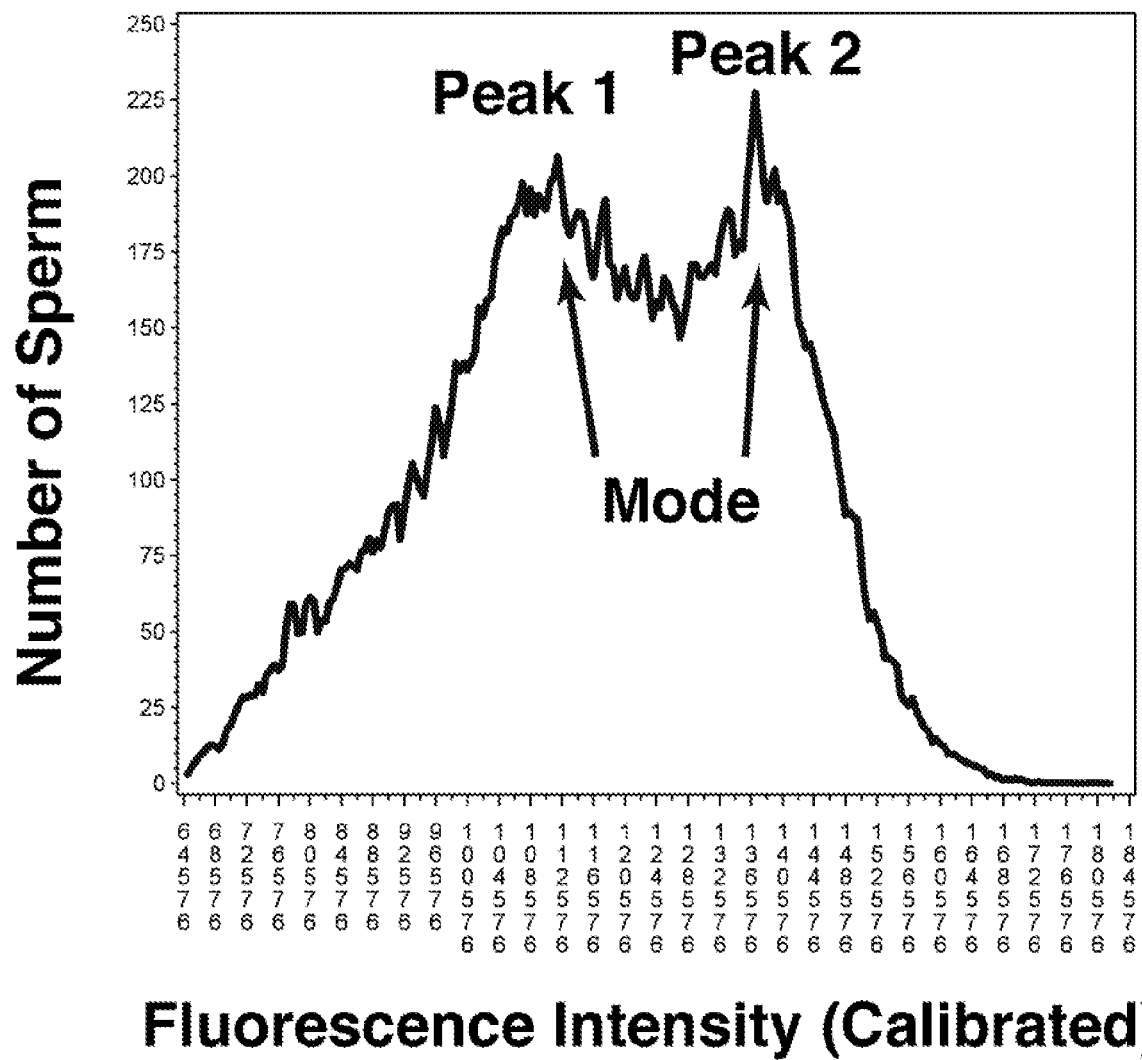
FIG. 7 shows flow cytometer output for 1 bull, demonstrating that sperm stained with HOECHST® 33342 have 2 peak intensities; these peaks relate to orientation of sperm passing through the detectors; the mode is indicated for peak 1 and peak 2.

An aliquot of the sample (75 µl) was mixed with 1425 µl of Dulbecco's PBS and run on the flow cytometer until at least 20,000 sperm cells were evaluated. The unwashed sample was simply diluted with Dulbecco's PBS after staining. Removing excess stain with the washing procedure similar to that done for microscopy analysis was found to provide better separation of high and low fertility bull semen samples and so the procedure that was used to obtain the results that are further discussed. A typical output is shown in FIG. 7 and demonstrates that 2 peaks are present. We will define the lower intensity peak as peak 1 and the higher intensity peak as peak 2. The 2 peaks represent different orientation of sperm as they are detected by the system. The distribution of sperm in each peak is also a function of the speed at which the sperm are traveling through the flow cytometer; therefore, a standard speed must be used.

Quantifying the peak intensity of each peak proved difficult as peaks are not symmetrical and substantial variation in sperm exist. Thus the mean and median were considered less useful for analysis. However, the mode of the lower intensity peak, peak 1, was 96,400±1005 for 51 high fertility bulls and 98,283±873 for 54 lower fertility bulls with a trend for the lower fertility bulls having a higher mode value, p=0.08. For the higher intensity peak, peak 2, the mode was similar between the 2 fertility groups. It is expected that better modeling and processing of the peak data, including smoothing of the curve for example, will produce more accurate values for the modes and will result in a better relationship to fertility. As anticipated, the orientation of sperm passing through the flow cytometer was a problem. In some embodiments, this may be resolved by using a flow orienting nozzle such as that used for sorting x or y bearing sperm on the flow cytometer.

Example 5

Additional Species

In various embodiments, a correlation between sperm DNA staining intensity and male fertility will be evaluated for other species including dogs and stallions. Preliminary trials have already found that staining can be evaluated in the same manner in dogs and stallion semen as has been used for bull and boar semen. For obtaining final data for dogs and stallions, samples of semen will be sought from males of each species having at least 25 breedings via artificial insemination for which conception rate data is available. These are expected to come from commercial semen banks for dogs and from breeders selling semen from stallions. In these and other species, breedings will likely be based on lifetime records as it is unlikely to get any male with sufficient numbers of breedings in a single year. In the United States, dogs and stallions do not suffer seasonal infertility as has been described herein for boars due to restricted breeding seasons (horses) or housing conditions (dogs).

It is expected that dogs, stallions, and other species will show the same correlation between increased DNA staining intensity and decreased male fertility as seen in bulls and boars.

References—Each of the following references is incorporated herein by reference in its entirety:

Parrish J J, Ostermeier. Fourier harmonic analysis of sperm morphology. 1998. $17^{th}$ Meeting of the National Association of Animal Breeders, Columbia Mo. Pp. 25-313.

Parrish J J, Enwall L, Kaya A, Pawshe C, Siddiqui M A, Shamusuddin M. Sperm shape research: an update. 2006. $21^{st}$ Meeting of the National Association of Animal Breeders, Columbia Mo. pp. 19-26.

Eid L N, Lorton S P, Parrish J J. Paternal influence of S-phase in the first cell cycle of the bovine embryo. Biol. Reprod. 1994.51:1232-1237.

Parrish J J, Eid L. In vitro fertilization and its relationship to bull fertility. 1994. $15^{th}$ Meeting of the National Association of Animal Breeders, Columbia Mo. pp. 68-73.

Parrish J J, Schindler J, Willenburg K, Enwall L, Kaya A. Quantitative sperm shape analysis: What can this tell us about male fertility. 2012. $24^{th}$ Meeting of the National Association of Animal Breeders, Columbia Mo. (in Press).

Zwald N R, Weigel K A, Chang Y M, Welper R D Clay J S. Genetic selection for health traits using producer-recorded data. II. Genetic correlations, disease probabilities, and relationships with existing traits. Journal of dairy science 2004a, 87:4295-4302.

Zwald N R, Weigel K A, Chang Y M, Welper R D, Clay J S. Genetic selection for health traits using producer-recorded data. I. Incidence rates, heritability estimates, and sire breeding values. Journal of dairy science 2004b, 87:4287-4294.

Peddinti D, Nanduri B, Kaya A, Feugang J M, Burgess S C, Memili E. Comprehensive proteomic analysis of bovine spermatozoa of varying fertility rates and identification of biomarkers associated with fertility. BMC Syst Biol. 2008, Feb 22;2:19. doi: 10.1186/1752-0509-2-19.m Flowers W L. Management of boars for efficient semen production. J. Reprod. Fertil. Suppl. 1997, 52:67-78.

Gibbs K M, Schindler J R, Parrish J J. Determining the effect of scrotal insulation on sperm production in the boar. J. Anim. Sci. E-suppl. 2013, 91:591.

Haralick R M, Shanmugam K, Dinstein I. Texture parameters for image classification, IEEE Trans SMC 3. 1973, 610-621.

Parrish J J. Bovine in vitro fertilization: In vitro oocyte maturation and sperm capacitation with heparin. Theriogenology 2014, 81:67-73.

Various features and advantages of the invention are set forth in the following claims.

What is claimed is:

1. A method for evaluating sperm fertility, the method comprising:
   (a) gathering a plurality of samples of sperm from a plurality of animals of the same species whose individual fertility is known, and
      (i) calculating a mean fertility and a standard deviation of fertility for the plurality of samples, and
      (ii) selecting from among the plurality of samples individual samples whose fertility is at least one standard deviation above the mean fertility and one standard deviation below the mean fertility calculated in step (a)(i), and
      (iii) designating the individual samples from step (a)(ii) whose fertility is at least one standard deviation above the mean fertility as "high-fertility sperm samples" and designating the individual samples from step (a)(ii) whose fertility is at least one standard deviation below the mean fertility as "low-fertility sperm samples";
   (b) for each individual sample in the high-fertility sperm samples and the low-fertility sperm samples:
      (i) staining the sample with a fluorescent DNA (deoxyribonucleic acid)-binding dye;
      (ii) fixing the sample with a fixation agent;
      (iii) collecting at least one fluorescence image of the stained and fixed sample;
      (iv) determining from the fluorescence image an edge of a nucleus in at least one sperm cell within the stained and fixed sample
      (v) measuring from the fluorescence image fluorescence intensity of the DNA-binding dye within an area defined by the edge of the nucleus in the at least one sperm cell and calculating an average fluorescence intensity per unit area in the area defined by the edge of the nucleus; and then
   (c) compiling the average fluorescence intensities per unit area for samples in the high-fertility sperm samples and the low-fertility sperm samples as calculated in step (b)(v) into standard curves of average fluorescence intensities per unit area values versus fertility for the high-fertility sperm samples and average fluorescence intensities per unit area values versus fertility for the low-fertility sperm samples; and then
   (d) repeating steps (b)(i) through (b)(v) for a sperm sample taken from a test animal of the same species as in step (a) whose fertility is unknown to yield an average fluorescence intensity per unit area value for the test animal; and
   (e) comparing the average fluorescence intensity per unit area value of the test animal to the standard curves of step (c), wherein when the average fluorescence intensity per unit area value for the test animal falls within the standard curve for the high-fertility sperm samples, the sperm of the test animal has a statistically significant better-than-mean fertility and when the average fluorescence intensity per unit area value for the test animal falls within the standard curve for the low-fertility sperm samples, the sperm of the test animal has a statistically significant worse-than-mean fertility.

2. The method of claim 1, wherein step (b)(1) comprises staining the sample with 2'-(4-ethoxyphenyl)-5-(4-methyl-1-piperazinyl)-2,5'-bi-1H-benzimidazole.

3. The method of claim 1, further comprising, in step (b)(ii), applying the stained sample to a substrate.

4. The method of claim 3, wherein the nucleus of the at least one sperm within the stained and fixed sample comprises a flattened oval and wherein the flattened portion is adjacent to the substrate.

5. The method of claim 1, wherein step (a) comprises gathering a plurality of samples of sperm from a plurality of animals selected from the group consisting of a bull, a boar, a human, a horse, a ram, and a dog.

6. The method of claim 1, wherein step (b)(iii) further comprises deconvoluting the at least one image to remove out-of-focus information.

7. A method for evaluating sperm fertility, the method comprising
   (a) gathering a plurality of samples of sperm from a plurality of animals of the same species whose individual fertility is known, and
      (i) calculating a mean fertility and a standard deviation of fertility for the plurality of samples, and
      (ii) selecting from among the plurality of samples individual samples whose fertility is at least one standard deviation above the mean fertility and one standard deviation below the mean fertility calculated in step (a)(i), and
      (iii) designating the individual samples from step (a)(ii) whose fertility is at least one standard deviation above the mean fertility as "high-fertility sperm samples" and designating the individual samples from step (a)(ii) whose fertility is at least one standard deviation below the mean fertility as "low-fertility sperm samples";
   (b) for each individual sample in the high-fertility sperm samples and the low-fertility sperm samples:
      (i) staining the sample with a fluorescent deoxyribonucleic acid (DNA)-binding dye;
      (ii) collecting fluorescence intensity measurements of the stained sample;
      (iii) calculating an average fluorescence intensity per unit area for the fluorescence intensity measurements of step (b)(ii);
      (iv) determining from the fluorescence image an edge of a nucleus in at least one sperm cell within the stained and fixed sample; and
      (v) measuring from the fluorescence image fluorescence intensity of the DNA-binding dye within an area defined by the edge of the nucleus in the at least one sperm cell and calculating an average fluorescence intensity per unit area in the area defined by the edge of the nucleus; and then
   (c) compiling the average fluorescence intensities per unit area for samples in the high-fertility sperm samples and the low-fertility sperm samples as calculated in step (b)(v) into standard curves of average fluorescence intensities per unit area values versus fertility for the high-fertility sperm samples and average fluorescence intensities per unit area values versus fertility for the low-fertility sperm samples; and then
   (d) repeating steps (b)(i) through (b)(v) for a sperm sample taken from a test animal of the same species as in step (a) whose fertility is unknown to yield an average fluorescence intensity per unit area value for the test animal; and
   (e) comparing the average fluorescence intensity per unit area value of the test animal to the standard curves of step (c), wherein when the average fluorescence intensity per unit area value for the test animal falls within the standard curve for the high-fertility sperm samples, the sperm of the test animal has a statistically significant better-than-mean fertility and when the average fluorescence intensity per unit area value for the test animal falls within the standard curve for the low-fertility sperm samples, the sperm of the test animal has a statistically significant worse-than-mean fertility.

8. The method of claim 7, wherein step (b)(1) comprises staining the sample with 2'-(4-ethoxyphenyl)-5-(4-methyl-1-piperazinyl)-2,5'-bi-1H-benzimidazole.

9. The method of claim 7, wherein step (a) comprises gathering a plurality of samples of sperm from a plurality of animals selected from the group consisting of a bull, a boar, a human, a horse, a ram, and a dog.

10. The method of claim 7, wherein step (b)(ii) comprises collecting the fluorescence intensity measurements of the stained sample using flow cytometry.

* * * * *